United States Patent [19]
Fontaine et al.

[11] Patent Number: 5,989,895
[45] Date of Patent: Nov. 23, 1999

[54] β-(1-3)-GLUCANOSYLTRANSFERASE, OLIGONUCLEOTIDES ENCODING THIS ENZYME, AND MOLECULES HAVING EFFECTS ON THIS ENZYME

[75] Inventors: Thierry Fontaine, Issy les Moulineaux, France; Robbert Hartland, Willetton, Australia; Isabelle Mouyna, Paris; Jean-Paul Latge, Issy les Moulineauz, both of France

[73] Assignee: Institut Pasteur, France

[21] Appl. No.: 08/922,171

[22] Filed: Sep. 2, 1997

Related U.S. Application Data

[60] Provisional application No. 60/024,910, Aug. 30, 1996, abandoned.

[51] Int. Cl.$^6$ .............. C12N 15/54; C12N 9/10; C12N 1/21; C12N 15/70

[52] U.S. Cl. .................. 435/252.33; 536/23.1; 536/23.2; 435/320.1; 435/252.3; 435/193

[58] Field of Search .................. 536/23.1, 23.2; 435/320.1, 252.3, 252.33, 193

*Primary Examiner*—Rebecca E. Prouty
*Attorney, Agent, or Firm*—Bierman, Muserlian and Lucas

[57] ABSTRACT

Protein having a β-(1–3) glucanosyltransferase activity. This protein can be used for screening molecules for their antifungal activities.

4 Claims, 11 Drawing Sheets

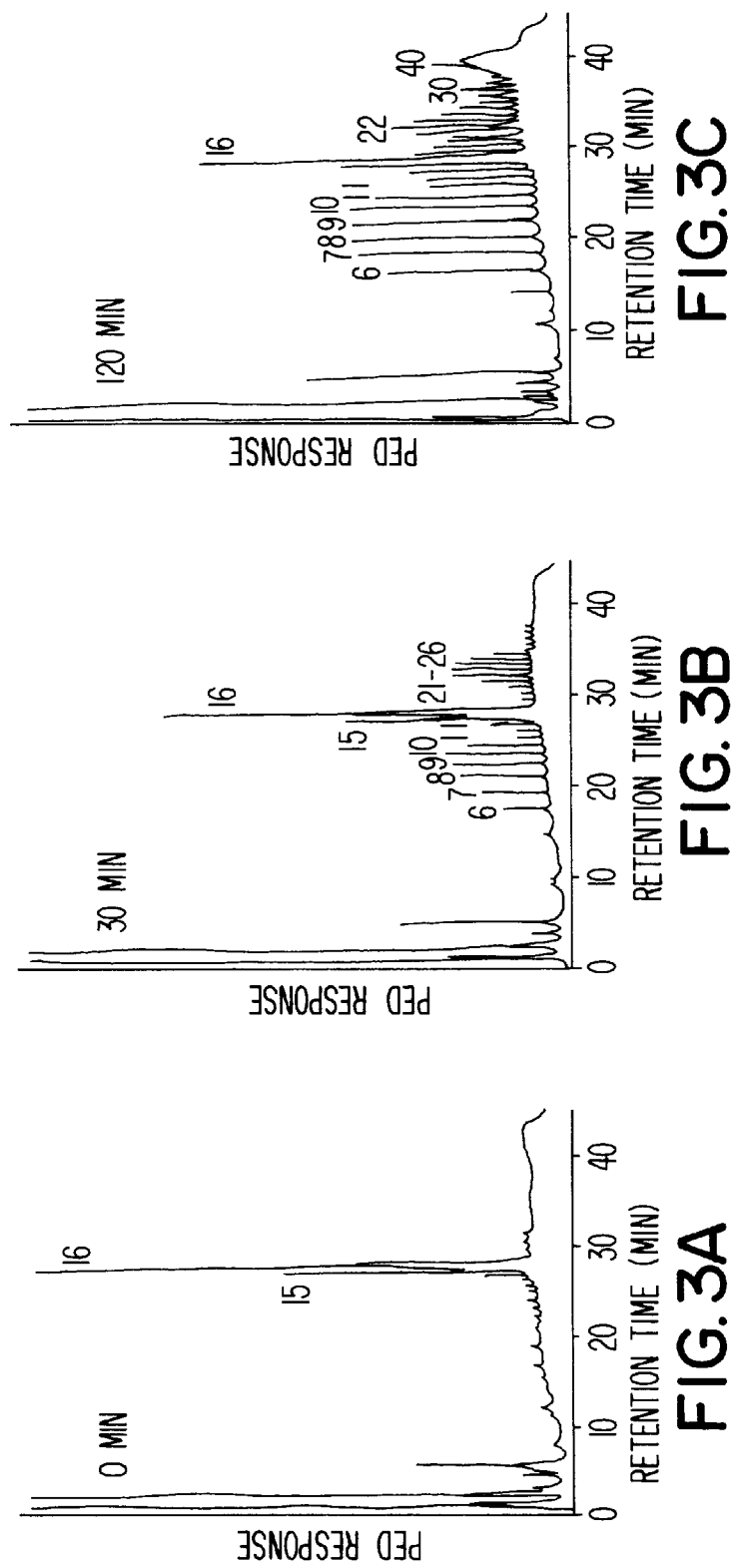

```
S   ..MLFKSLSKLATAA....AFFAGVAT..ADDVPAIEVVGNKFFYSNNGSQFYIRGVAYQ
C   MYSLIKSLATFATFA....TLFSLTLAKFESSTPPVEVVGNKFYFSNNGSQFLIRGIAYQ
A   ....MKASAVTAALAVGASTVLAAPSIKARDDVTPITMKGNAFF..KGDERFYIRGVDYQ

S   ADIANETSGS.......TVNDPLANYESCSRDIPYLKKLNTNVIRVYAINTTLDHSECMK
C   QDAAGSVSSGYDADPNRKYNDPLADRDACKRDVKYFKESNTNTLRVYAIDPDKDHEECMK
A   PGGSSD...........LADPIADADGCKRDIAKFKELGLNTIRVYSVDNSKNHDECMN

S   ALNDADIYVIADLAAPATSINRDDP.TWTVDLFNSYK.TVVDTFANYINVLGFFAGNEVT
C   IFSDAGIYIVADLSEPTVSINRNNP.EWNLDLYKRYT.KVIDKMQEYSNVLGFFAGNEVT
A   TLADAGIYLVLDVNTPKYSINRAKPKESYNDVYLQYIFATVDAFAGYKNTLAFFSGNEVI

S   NNYINTDASAFVKAAIRDVRQYISDKNYRKIPVGYSS..................NDD
C   NNRSNTDASAFVKAAIRDMKKYIKESDYRQIPVGYSS..................NDD
A   NDGPSSSAAPYVKAVTRDLRQYIRSRKYREIPVGYSAVSSSATSW*FVTSC*LVHT*ADI
                                         ←――――――― I₁ ―――――――→

S   EDTRVKMIDYFACGDDDVKADFYGINMYEWCGKSDFKTSGYADRTAEFKNLSIPVFFSEY
C   EEIRVAIADYFSCGSLDDRADFFGINMYEWCGKSTFETSGYKDRTEEIKNLTIPAFFSEY
A   DTNRLQMAQYMNCGSDDERSDFFAFNDYSWCDPSSFKTSGWDQKVKNFTGYGLPLFLSEY

S   GCNEVTPRLFITEVEALYGSNMTDVWSGGIVYMYFEEINKYGLVSIDGNDVKTLDDFNNYS
C   GCNANRPRLFQEIGTLYSDKMTDVWSGGIVYMYFEEANKYGLVLVDGNSVKTLSDYNNYK
A   GCNTNK.RQFQEVSSLYSTDMTGVYSGGLVYEYSQEASNYGLVEISGNNVKELPDFDALK

S   SEINKISPTSANTK..SYSATTSDVACPAT.GKYWSAATELPPTPNGGLCSCMNAANSCV
C   SEMNKISPSLAHTSTLSSSDASKTLQCPGTAASTWKAATNLPPTPDESYCDCISKSLECV
A   TAFEKTSNPSGDGN...YNKTGGANPCPAKDAPNWDVD.......NDALPAIPEPAKKYM

S   VSDDVDSDDYETLFNWICNEVDCSGISANGTAGKYGAYSFCTPKEQLSFVMNLYYEKSGG
C   VADDVDKEDYGDLFGQVCGYIDCSAISADGSKGEYGVASFCSDKDRLSYVLNQYYLDQDK
A   TEGAGKGPGFA.................................................

S   SKSDCSFSGSATLQTATTQASCSSALKEIGSMGTNSASGSVDLGSGTESSTASSNASGSS
C   KSSACDFKGSASIN...SKASASGSCKAVSGVATGKAS.....SSGGSSKSGSSSASASG
A   ..........................................GPGSQDRGTQSTATAEPGSGSATGSS

S   SKSNSGSSSGSSSSSSSSSSKKNAATNVKANLAQVVFTSIISLFIAAGVGFALV.
C   SSSSSTSSGSSSSS........GVKATQQMSMVKLVSIITIVTAFVGGMSVVF
A   SSGTSTSSKGAAAGL........TVPSLTMAPVVVGAVTLLSTVFGAGLVLL*
```

FIG. 7

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1418
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION:1..1418

(xi) SEQUENCE DESCRIPTION: SEQ ID NO: 1:

```
ATGAAGGCCT CTGCTGTTAC TGCCGCTCTC GCCGTCGGTG                    40

CTTCCACCGT TCTGGCAGCC CCCTCCATCA AGGCTCGTGA                    80

CGACGTTACT CCCATCACTG TCAAGGGCAA TGCCTTCTTC                   120

AAGGGCGATG AGCGTTTCTA TATTCGCGGT GTCGACTACC                   160

AGCCCGGTGG CTCCTCCGAC CTGGCTGATC CCATCGCTGA                   200

TGCCGATGGT TGCAAGCGTG ACATTGCCAA GTTCAAGGAG                   240

CTGGGCCTGA ACACTATCCG TGTCTACTCG GTCGACAACT                   280

CCAAGAACCA CGATGAGTGT ATGAATACAC TGGCTGATGC                   320

TGGCATCTAT CTGGTGCTCG ATGTCAACAC TCCCAAGTAC                   360

TCCATCAACC GCGCCAAGCC TAAGGAGTCG TACAACGATG                   400
```

-continued

| | |
|---|---|
| TCTACCTCCA GTATATCTTC GCTACCGTTG ATGCTTTCGC | 440 |
| CGGTTACAAG AACACCCTCG CTTTCTTCTC CGGCAACGAG | 480 |
| GTTATCAACG ATGGCCCTTC CTCCTCTGCT GCTCCCTACG | 520 |
| TCAAGGCCGT CACTCGTGAT CTGCTCAGTA CATCCGTAGC | 560 |
| CGCAAGTACC GTGAGATTCC TGTCGGCTAC TCGGCTGTAA | 600 |
| GTTCCTCTGC TACATCCTGG TGATTCGTGA CTTCTTGTTG | 640 |
| ACTAGTCCAT ACCTAGGCCG ATATCGACAC CAACCGTCTT | 680 |
| CAGATGGCCC AGTATATGAA CTGCGGTTCC GACGACGAGC | 720 |
| GCAGTGACTT CTTCGCTTTC AACGACTACT CCTGGTGCGA | 760 |
| TCCCTCCTCT TTCAAAACCT CGGGCTGGGA TCAGAAGGTC | 800 |
| AAGAACTTCA CTGGCTACGG TCTTCCTCTC TTCCTGTCCG | 840 |
| AATACGGCTG CAACACCAAC AAGCGTCAAT TCCAAGAAGT | 880 |
| CAGCTCTCTC TACTCCACGG ACATGACTGG TGTCTACTCT | 920 |
| GGTGGTCTCG TGTACGAGTA CTCTCAGGAG GCCAGCAACT | 960 |
| ACGGTCTGGT GGAGATTAGC GGCAACAATG TCAAGGAGCT | 1000 |
| CCCAGACTTC GACGCTCTGA AGACCGCGTT CGAAAAGACC | 1040 |
| TCCAACCCCT CCGGCGACGG CAACTACAAC AAGACTGGTG | 1080 |
| GTGCCAACCC TTGCCCCGCT AAGGACGCTC CCAACTGGGA | 1120 |
| CGTTGACAAC GATGCTCTTC CTGCCATCCC CGAGCCCGCC | 1160 |
| AAGAAGTACA TGACTGAGGG TGCTGGCAAG GGCCCTGGTT | 1200 |
| TTGCCGGACC TGGCAGCCAG GACCGTGGTA CCCAGTCCAC | 1240 |
| TGCCACTGCT GAGCCCGGAT CTGGCTCTGC CACTGGAAGC | 1280 |
| AGCAGCAGCG GCACCTCCAC CTCTTCCAAG GGCGCTGCAG | 1320 |
| CTGGCCTGAC TGTCCCTAGC CTGACCATGG CTCCCGTTGT | 1360 |
| CGTTGGTGCG GTTACACTCC TGTCCACCGT CTTCGGCGCT | 1400 |
| GGCCTCGTCC TCTTGTGA | 1418 |

(2) INFORMATION FOR SEQ ID NO: 2:

(i) SEQUENCE CHARACTERISTICS:
        (A) LENGTH: 472
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 2:

Met Lys Ala Ser Ala Val Thr Ala Ala Leu Ala Val
1             5                   10

Gly Ala Ser Thr Val Leu Ala Ala Pro Ser Ile Lys
           15                20

Ala Arg Asp Asp Val Thr Pro Ile Thr Val Lys Gly
25             30              35

Asn Ala Phe Phe Lys Gly Asp Glu Arg Phe Tyr Ile
           40                45

-continued

```
Arg Gly Val Asp Tyr Gln Pro Gly Ser Ser Asp
 50                  55                  60

Leu Ala Asp Pro Ile Ala Asp Ala Asp Gly Cys Lys
             65                  70

Arg Asp Ile Ala Lys Phe Lys Glu Leu Gly Leu Asn
         75                  80

Thr Ile Arg Val Tyr Ser Val Asp Asn Ser Lys Asn
 85                  90                  95

His Asp Glu Cys Met Met His Trp Leu Met Leu Ala
            100                 105

Ser Ile Trp Cys Ser Met Ser Thr Leu Pro Ser Thr
        110                 115                 120

Pro Ser Thr Ala Pro Ser Leu Arg Ser Arg Thr Thr
                125                 130

Met Ser Thr Ser Ser Ile Ser Ser Leu Pro Leu Met
            135                 140

Leu Ser Pro Val Thr Arg Thr Pro Ser Leu Ser Ser
145                 150                 155

Pro Ala Thr Arg Leu Ser Thr Met Ala Leu Pro Pro
                160                 165

Leu Leu Leu Pro Thr Ser Arg Pro Ser Leu Val Ile
170                 175                 180

Cys Val Ser Thr Ser Val Ala Ala Ser Thr Val Arg
                185                 190

Phe Leu Ser Ala Thr Arg Leu Glx Val Pro Leu Leu
            195                 200

His Pro Gly Asp Ser Glx Leu Leu Cys Glx Leu Val
205                 210                 215

His Thr Glx Ala Asp Ile Asp Thr Asn Arg Leu Gln
            220                 225

Met Ala Gln Tyr Met Asn Cys Gly Ser Asp Asp Glu
            230                 235                 240

Arg Ser Asp Phe Phe Ala Phe Asn Asp Tyr Ser Trp
                245                 250

Cys Asp Pro Ser Ser Phe Lys Thr Ser Gly Trp Asp
                255                 260

Gln Lys Val Lys Asn Phe Thr Gly Tyr Gly Leu Pro
265                 270                 275

Leu Phe Leu Ser Glu Tyr Gly Cys Asn Thr Asn Lys
            280                 285

Arg Gln Phe Gln Glu Val Ser Ser Leu Tyr Ser Thr
            290                 295                 300

Asp Met Thr Gly Asp Tyr Ser Gly Gly Leu Val Tyr
                305                 310

Glu Tyr Ser Gln Glu Ala Ser Asn Tyr Gly Leu Val
            315                 320

Glu Ile Ser Gly Asn Asn Asp Lys Glu Leu Pro Asp
325                 330                 335

Phe Asp Ala Leu Lys Thr Ala Phe Glu Lys Thr Ser
                340                 345

Asn Pro Ser Gly Asp Gly Asn Tyr Asn Lys Thr Gly
            350                 355                 360

Gly Ala Asn Pro Cys Pro Ala Lys Asp Ala Pro Asn
                365                 370
```

```
Trp Asp Val Asp Asn Asp Ala Leu Pro Ala Ile Pro
        375                 380

Glu Pro Ala Lys Lys Tyr Met Thr Glu Gly Ala Gly
385                 390                 395

Lys Gly Pro Gly Phe Ala Gly Pro Gly Ser Gln Asp
            400                 405

Arg Gly Thr Gln Ser Thr Ala Thr Ala Glu Pro Gly
    410                 415                 420

Ser Gly Ser Ala Thr Gly Ser Ser Ser Ser Gly Thr
                425                 430

Ser Thr Ser Ser Lys Gly Ala Ala Gly Leu Thr
            435                 440

Val Pro Ser Leu Thr Met Ala Pro Val Val Val Gly
445                 450                 455

Ala Val Thr Leu Leu Ser Thr Val Phe Gly Ala Gly
            460                 465

Leu Val Leu Leu
    470
```

(2) INFORMATION FOR SEQ ID NO: 3:

(i) SEQUENCE CHARACTERISTICS:
        (A) LENGTH: 446
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 3:

```
Asp Asp Val Thr Pro Ile Thr Val Lys Gly Asn Ala
1               5                   10

Phe Phe Lys Gly Asp Glu Arg Phe Tyr Ile Arg Gly
        15                  20

Val Asp Tyr Gln Pro Gly Gly Ser Ser Asp Leu Ala
25              30                  35

Asp Pro Ile Ala Asp Ala Asp Gly Cys Lys Arg Asp
            40                  45

Ile Ala Lys Phe Lys Glu Leu Gly Leu Asn Thr Ile
    50                  55                  60

Arg Val Tyr Ser Val Asp Asn Ser Lys Asn His Asp
                65                  70

Glu Cys Met Met His Trp Leu Met Leu Ala Ser Ile
            75                  80

Trp Cys Ser Met Ser Thr Leu Pro Ser Thr Pro Ser
85                  90                  95

Thr Ala Pro Ser Leu Arg Ser Arg Thr Thr Met Ser
            100                 105

Thr Ser Ser Ile Ser Ser Leu Pro Leu Met Leu Ser
    110                 115                 120

Pro Val Thr Arg Thr Pro Ser Leu Ser Ser Pro Ala
            125                 130

Thr Arg Leu Ser Thr Met Ala Leu Pro Pro Leu Leu
        135                 140
```

```
Leu Pro Thr Ser Arg Pro Ser Leu Val Ile Cys Val
145                 150                 155

Ser Thr Ser Val Ala Ala Ser Thr Val Arg Phe Leu
            160                 165

Ser Ala Thr Arg Leu Glx Val Pro Leu Leu His Pro
        170                 175                 180

Gly Asp Ser Glx Leu Leu Cys Glx Leu Val His Thr
                185                 190

Glx Ala Asp Ile Asp Thr Asn Arg Leu Gln Met Ala
            195                 200

Gln Tyr Met Asn Cys Gly Ser Asp Asp Glu Arg Ser
205                 210                 215

Asp Phe Phe Ala Phe Asn Asp Tyr Ser Trp Cys Asp
                220                 225

Pro Ser Ser Phe Lys Thr Ser Gly Trp Asp Gln Lys
        230                 235                 240

Val Lys Asn Phe Thr Gly Tyr Gly Leu Pro Leu Phe
                245                 250

Leu Ser Glu Tyr Gly Cys Asn Thr Asn Lys Arg Gln
            255                 260

Phe Gln Glu Val Ser Ser Leu Tyr Ser Thr Asp Met
265                 270                 275

Thr Gly Asp Tyr Ser Gly Gly Leu Val Tyr Glu Tyr
            280                 285

Ser Gln Glu Ala Ser Asn Tyr Gly Leu Val Glu Ile
    290                 295                 300

Ser Gly Asn Asn Asp Lys Glu Leu Pro Asp Phe Asp
                305                 310

Ala Leu Lys Thr Ala Phe Glu Lys Thr Ser Asn Pro
        315                 320

Ser Gly Asp Gly Asn Tyr Asn Lys Thr Gly Gly Ala
325                 330                 335

Asn Pro Cys Pro Ala Lys Asp Ala Pro Asn Trp Asp
            340                 345

Val Asp Asn Asp Ala Leu Pro Ala Ile Pro Glu Pro
350                 355                 360

Ala Lys Lys Tyr Met Thr Glu Gly Ala Gly Lys Gly
                365                 370

Pro Gly Phe Ala Gly Pro Gly Ser Gln Asp Arg Gly
        375                 380

Thr Gln Ser Thr Ala Thr Ala Glu Pro Gly Ser Gly
385                 390                 395

Ser Ala Thr Gly Ser Ser Ser Gly Thr Ser Thr
            400                 405

Ser Ser Lys Gly Ala Ala Gly Leu Thr Val Pro
        410                 415                 420

Ser Leu Thr Met Ala Pro Val Val Gly Ala Val
                425                 430

Thr Leu Leu Ser Thr Val Phe Gly Ala Gly Leu Val
            435                 440

Leu Leu
445
```

(2) INFORMATION FOR SEQ ID NO: 4:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: mutation
        (B) LOCATION:replace(6, "c")

(ix) FEATURE:
        (A) NAME/KEY: mutation
        (B) LOCATION:replace(9, "t")

(ix) FEATURE:
        (A) NAME/KEY: mutation
        (B) LOCATION:replace(12, "c")

(ix) FEATURE:
        (A) NAME/KEY: mutation
        (B) LOCATION:replace(18, "t")

(ix) FEATURE:
        (A) NAME/KEY: mutation
        (B) LOCATION:replace(24, "c")

(ix) FEATURE:
        (A) NAME/KEY: mutation
        (B) LOCATION:replace(27, "c")

(ix) FEATURE:
        (A) NAME/KEY: mutation
        (B) LOCATION:replace(33, "c")

(xi) SEQUENCE DESCRIPTION: SEQ ID NO: 4:

```
AAGGGTAACG CTTTCTTCAA GGGTGATGAG CGTTTCTA                    38
```

(2) INFORMATION FOR SEQ ID NO: 5:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 5:

```
GAATTCGACG ACGTTACTCC CATCACT                                27
```

(2) INFORMATION FOR SEQ ID NO: 6:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 6:

```
TCTAGAGGGT ATGAGAAGAA CAAATCA                                27
```

β-(1-3)-GLUCANOSYLTRANSFERASE, OLIGONUCLEOTIDES ENCODING THIS ENZYME, AND MOLECULES HAVING EFFECTS ON THIS ENZYME

This application claims the benefit of provisional application Ser. No. 60/024,910 filed Aug. 30, 1996, now abandoned.

The present invention relates to a protein having a glucanosyltransferase activity, and more particularly a β-(1–3) glucanosyltransferase activity.

The present invention is also related with oligonucleotides encoding this protein having an enzymatic activity.

It beaidc relates to molecules having an effect on the activity of this enzyme.

Opportunistic fungal infections due to Candida, Aspergillus, Cryptococcus and Pneumocystis are responsible for increased morbidity and mortality among AIDS and other patients clinically immunocompromised. In addition, Candida and dermatophytes remain today an important medical problem amongst immunocompetent patients. Despite the increasing number of infections due to pathogenic and opportunistic fungi, therapy for mycoses had not improved much in recent years. Two family of drugs are used:azoles and Amphotericin B. These agents show some drawbacks since Amphotericin B treatment is associated with nephrotoxicity and azoles are more fungistatic than fungicidal.

Fungi are eucaryotic microorganisms which share most biochemical pathways with their host with one main exception: the cell wall biosynthesis. The cell wall is a rigid shell which protects the cell against environmental and mechanical stresses but also a dynamic structure which is involved in transport of ions and macromolecules and localization of enzymes involved in fungal growth. Consequently disruption of the cell wall organization should be deleterious to the fungus.

The fungal cell wall skeleton is mainly composed of polysaccharide polymers (β(1–3) glucans, mannans, chitin) which are not found in humans. For this reason, cell wall biosynthesis has been a target for the search of new antifungal drugs. Penicillins and cephalosporins which are both bacterial cell wall inhibitors and potent antibiotics bring credibility to this hypothesis. In addition, several molecules which inhibit fungal cell wall development have antifungal properties (Debono and Gordee, 1994. Annu. Rev. Microbiol, 48, 471–497). Amongst them, one can cite:

1) The echinocandin lipopeptide and papulacandin glycopeptide families which are non-competitive inhibitors of the glucan synthase complex.

2) The polyoxins and nikkomycins which are analogs of UDP-GlcNac and potent competitive inhibitors of chitin synthase, and 3) The mannan-binding pradimicins and benanomicins.

The synthesis of the β(1–3) glucan and chitin is under the control of enzyme complexes (glucan synthase and chitin synthase) which are localized at the plasma membrane level. Once the polymers are extruded the polymers occurs and is responsible for the rigidity of the cell wall. The proteins and genes of the glucan and chitin synthases begin to be understood quite well.

But inhibition of chitin and glucan synthases by a molecule requires three steps: the transport through the cell wall, the crossing of the plasma membrane and the transport into the cell toward the target site, any step that can be responsible for the failure of the enzyme inhibitor to be an efficient antifungal drug as well as for selection of resistance towards the drug.

The transferases which are responsible of the establishment of covalent linkages between the different wall polymers have been poorly studied until now.

Such enzymes represent a better target than the glucan and chintin synthase complexes since they are of an easier access to a putative anti fungal drug.

Nuoffer et al. (1991, Mol. Cell. Biol., 11, 27–37) described a glycoprotein, called Gas1p, exposed on the surface of *Saccharomyces cerevisiae*. The gene encoding this protein has been cloned. The function of Gas1p is not essential for cell viability, and has not been determined.

Saporito-Irwing et al (1995, Mol. Cell. Biol., 15, 601–613) isolated a gene from *Candida albicans*, designated PHR1. The predicted aminoacid sequence of the PHR1 protein was 56% identical to that of the Gas1 protein. The gene is regulated in response to the pH of the culture medium. As for Cas1p no function was determined.

It is clear from the analysis of the prior art, that there was existing a problem which is to obtain molecules having an efficient anti fungal activity.

The inventors have solved this problem.

They have shown that the introduction of mutations in a glucanosyltransferase from *Aspergillus fumigatus* prevents the development of this microorganism, in particular at an acidic pH.

They have moreover determined the sequence of this enzyme.

The present invention is thus relative to a protein having a β-(1–3) glucanosyltranferase activity characterized in that it shows at least 50%, preferentially 60%, and more preferentially 85% of homology with the proteins having the sequences, or a part of the following sequences SEQ ID No2 or SEQ ID No3:

SEQ ID N°2:

Met Lys Ala Ser Ala Val Thr Ala Ala Leu Ala Val Gly

Ala Ser Thr Val Leu Ala Ala Pro Ser Ile Lys Ala Arg

Asp Asp Val Thr Pro Ile Thr Val Lys Gly Asn Ala Phe

Phe Lys Gly Asp Glu Arg Phe Tyr Ile Arg Gly Val Asp

Tyr Gln Pro Gly Gly Ser Ser Asp Leu Ala Asp Pro Ile

Ala Asp Ala Asp Gly Cys Lys Arg Asp Ile Ala Lys Phe

Lys Glu Leu Gly Leu Asn Thr Ile Arg Val Tyr Ser Val

Asp Asn Ser Lys Asn His Asp Glu Cys Met Met His Trp

Leu Met Leu Ala Ser Ile Trp Cys Ser Met Ser Thr Leu

Pro Ser Thr Pro Ser Thr Ala Pro Ser Leu Arg Ser Arg

Thr Thr Met Ser Thr Ser Ser Ile Ser Ser Leu Pro Leu

Met Leu Ser Pro Val Thr Arg Thr Pro Ser Leu Ser Ser

Pro Ala Thr Arg Leu Ser Thr Met Ala Leu Pro Pro Leu

Leu Leu Pro Thr Ser Arg Pro Ser Leu Val Ile Cys Val

Ser Thr Ser Val Ala Ala Ser Thr Val Arg Phe Leu Ser

Ala Thr Arg Leu Glx Val Pro Leu Leu His Pro Gly Asp

Ser Glx Leu Leu Cys Glx Leu Val His Thr Glx Ala Asp

Ile Asp Thr Asn Arg Leu Gln Met Ala Gln Tyr Met Asn

Cys Gly Ser Asp Asp Glu Arg Ser Asp Phe Phe Ala Phe

```
Asn Asp Tyr Ser Trp Cys Asp Pro Ser Ser Phe Lys Thr

Ser Gly Trp Asp Gln Lys Val Lys Asn Phe Thr Gly Tyr

Gly Leu Pro Leu Phe Leu Ser Glu Tyr Gly Cys Asn Thr

Asn Lys Arg Gln Phe Gln Glu Val Ser Ser Leu Tyr Ser

Thr Asp Met Thr Gly Asp Tyr Ser Gly Gly Leu Val Tyr

Glu Tyr Ser Gln GLu Ala Ser Asn Tyr Gly Leu Val Glu

Ile Ser Gly Asn Asn Asp Lys Glu Leu Pro Asp Phe Asp

Ala Leu Lys Thr Ala Phe Glu Lys Thr Ser Asn Peo Ser

Gly Asp Gly Asn Tyr Asn Lys Thr Gly Gly Ala Asn Pro

Cys Pro Ala Lys Asp Ala Pro Asn Trp Asp Val Asp Asn

Asp Ala Leu Pro Ala Ile Pro Glu Pro Ala Lys Lys Tyr

Met Thr Glu Gly Ala Gly Lys Gly Pro Gly Phe Ala Gly

Pro Gly Ser Gln Asp Arg Gly Thr Gln Ser Thr Ala Thr

Ala Glu Pro Gly Ser Gly Ser Ala Thr Gly Ser Ser Ser

Ser Gly Thr Ser Thr Ser Ser Lys Gly Ala Ala Ala Gly

Leu Thr Val Pro Ser Leu Thr Met Ala Pro Val Val Val

Gly Ala Val Thr Leu Leu Ser Thr Val Phe Gly Ala Gly

Leu Val Leu Leu

SEQ ID N°3:

Asp Asp Val Thr Pro Ile Thr Val Lys Gly Asn Ala Phe

Phe Lys Gly Asp Glu Arg Phe Tyr Ile Arg Gly Val Asp

Tyr Gln Pro Gly Gly Ser Ser Asp Leu Ala Asp Pro Ile

Ala Asp Ala Asp Gly Cys Lys Arg Asp Ile Ala Lys Phe

Lys Glu Leu Gly Leu Asn Thr Ile Arg Val Tyr Ser Val

Asp Asn Ser Lys Asn His Asp Glu Cys Met Met His Trp

Leu Met Leu Ala Ser Ile Trp Cys Ser Met Ser Thr Leu

Pro Ser Thr Pro Ser Thr Ala Pro Ser Leu Arg Ser Arg

Thr Thr Met Ser Thr Ser Ser Ile Ser Ser Leu Pro Leu

Met Leu Ser Pro Val Thr Arg Thr Pro Ser Leu Ser Ser

Pro Ala Thr Arg Leu Ser Thr Met Ala Leu Pro Pro Leu

Leu Leu Pro Thr Ser Arg Pro Ser Leu Val Ile Cys Val

Ser Thr Ser Val Ala Ala Ser Thr Val Arg Phe Leu Ser

Ala Thr Arg Leu Glx Val Pro Leu Leu His Pro Gly Asp

Ser Glx Leu Leu Cys Glx Leu Val His Thr Glx Ala Asp

Ile Asp Thr Asn Arg Leu Gln Met Ala Gln Tyr Met Asn

Cys Gly Ser Asp Asp Glu Arg Ser Asp Phe Phe Ala Phe

Asn Asp Tyr Ser Trp Cys Asp Pro Ser Ser Phe Lys Thr

Ser Gly Trp Asp Gln Lys Val Lys Asn Phe Thr Gly Tyr

Gly Leu Pro Leu Phe Leu Ser Glu Tyr Gly Cys Asn Thr

Asn Lys Arg Gln Phe Gln Glu Val Ser Ser Leu Tyr Ser

Thr Asp Met Thr Gly Asp Tyr Ser Gly Gly Leu Val Tyr

Glu Tyr Ser Gln Glu Ala Ser Asn Tyr Gly Leu Val Glu

Ile Ser Gly Asn Asn Asp Lys Glu Leu Pro Asp Phe Asp

Ala Leu Lys Thr Ala Phe Glu Lys Thr Ser Asn Pro Ser

Gly Asp Gly Asn Tyr Asn Lys Thr Gly Gly Ala Asn Pro

Cys Pro Ala Lys Asp Ala Pro Asn Trp Asp Val Asp Asn

Asp Ala Leu Pro Ala Ile Pro Glu Pro Ala Lys Lys Tyr

Met Thr Glu Gly Ala Gly Lys Gly Pro Gly Phe Ala Gly

Pro Gly Ser Gln Asp Arg Gly Thr Gln Ser Thr Ala Thr

Ala Glu Pro Gly Ser Gly Ser Ala Thr Gly Ser Ser Ser

Ser Gly Thr Ser Thr Ser Ser Lys Gly Ala Ala Ala Gly

Leu Thr Val Pro Ser Leu Thr Met Ala Pro Val Val Val

Gly Ala Val Thr Leu Leu Ser Thr Val Phe Gly Ala Gly

Leu Val Leu Leu
```

Preferentially, such a protein shows a molecular weight of almost 44 kD, or of almost 49 kD, if it brings at least one N-glycosyl rest.

The present invention is moreover related to some fragments of such protein.

The said invention is not limited to some proteins having the sequences SEQ ID NO2 or SEQ ID NO3, but extends to any protein showing sequences similarities with the proteins having the sequences SEQ ID NO2 or SEQ ID NO3, and in particular showing some amino acids substitutions in which an amino acid is replaced by an another amino acid having substantially the same physico-chemical features. The biochemistry manual of Lehninger (Flammarion Medecine-Science, 1977), or one of its recent reeditions distinguishes four groups of amino acids, on the basis of their physical-chemical behaviours: those with a non-polar or hydrophobic side chain, those with an unloaded polar side chain, those with a negatively loaded side chain, and those with a positively loaded side chain.

The present invention is moreover related to a nucleotodic sequence encoding a protein, or a protein fragment such as described hereabove, and more particularly a DNA (cDNA or genomic DNA) or a RNA sequence.

Such DNA sequence can be this showing an homology of at least 50%, preferentially 60%, and more preferentially 85% with the genomic sequence SEQ ID NO1, or a part of the following sequence SEQ ID NO1:

```
ATGAAGGCCTCTGCTGTTACTGCCGCTCTCGCCGTCGGTGCTTCCA

CCGTTCTGGCAGCCCCCTCCATCAAGGCTCGTGACGACGTTACTCC

CATCACTGTCAAGGGCAATGCCTTCTTCAAGGGCGATGAGCGTTTC

TATATTCGCGGTGTCGACTACCAGCCCGGTGGCTCCTCCGACCTGG

CTGATCCCATCGCTGATGCCGATGGTTGCAAGCGTGACATTGCCAA

GTTCAAGGAGCTGGGCCTGAACACTATCCGTGTCTACTCGGTCGAC

AACTCCAAGAACCACGATGAGTGTATGAATACACTGGCTGATGCTG

GCATCTATCTGGTGCTCGATGTCAACACTCCCAAGTACTCCATCAAC

CGCGCCAAGCCTAAGGAGTCGTACAACGATGTCTACCTCCAGTATA
```

-continued

```
TCTTCGCTACCGTTGATGCTTTCGCCGGTTACAAGAACACCCTCGC

TTTCTTCTCCGGCAACGAGGTTATCAACGATGGCCCTTCCTCCTCTG

CTGCTCCCTACGTCAAGGCCGTCACTCGTGATCTGCGTCAGTACAT

CCGTAGCCGCAAGTACCGTGAGATTCCTGTCGGCTACTCGGCTGTA

AGTTCCTCTGCTACATCCTGGTGATTCGTGACTTCTTGTTGACTAGT

CCATACCTAGGCCGATATCGACACCAACCGTCTTCAGATGGCCCAG

TATATGAACTGCGGTTCCGACGACGAGCGCAGTGACTTCTTCGCTT

TCAACGACTACTCCTGGTGCGATCCCTCCTCTTTCAAAACCTCGGG

CTGGGATCAGAAGGTCAAGAACTTCACTGGCTACGGTCTTCCTCTC

TTCCTGTCCGAATACGGCTGCAACACCAACAAGCGTCAATTCCAAG

AAGTCAGCTCTCTCTACTCCACGGACATGACTGGTGTCTACTCTGG

TGGTCTCGTGTACGAGTACTCTCAGGAGGCCAGCAACTACGGTCTG

GTGGAGATTAGCGGCAACAATGTCAAGGAGCTCCCAGACTTCGACG

CTCTGAAGACCGCGTTCGAAAAGACCTCCAACCCCTCCGGCGACG

GCAACTACAACAAGACTGGTGGTGCCAACCCTTGCCCCGCTAAGGA

CGCTCCCAACTGGGACGTTGACAACGATGCTCTTCCTGCCATCCCC

GAGCCCGCCAAGAAGTACATGACTGAGGGTGCTGGCAAGGGCCCT

GGTTTTGCCGGACCTGGCAGCCAGGACCGTGGTACCCAGTCCACT

GCCACTGCTGAGCCCGGATCTGGCTCTGCCACTGGAAGCAGCAGC

AGCGGCACCTCCACCTCTTCCAAGGGCGCTGCAGCTGGCCTGACT

GTCCCTAGCCTGACCATGGCTCCCGTTGTCGTTGGTGCGGTTACAC

TCCTGTCCACCGTCTTCGGCGCTGGCCTCGTCCTCTTGTGA
```

This sequence has been included in a 2,2 kb fragment, which has itself been included in the XbaI site of the pUC19 vector (Maniatis and al, 1989, Cold Spring Harbor Laboratories Press). The $DH_5\alpha$ E. coli strain bringing the vector modified in this way, has been deposited to the Collection Nationale de Culture Microorganismes de l'Institut Pasteur (CNCM) on Jul. 26, 1996 under the number I-1763.

Such a sequence can be also this showing an homology of at least 50%, preferentially 60%, and more preferentially 85% with the complementary DNA sequence comprised in a 1,4 kb fragment which has been included in the pCRII vector (In Vitrogen). The whole, brought by the $DH_5\alpha$ E. coli strain has been deposited to the Collection Nationale de Culture de Microorganismes de l'Institut Pasteur (CNCM) on Jul. 26, 1996 under the number noI-1762.

These two strains are some subjects of the present invention.

Such a protein can be obtained by purification from a Aspergillus fumigatus autolysate. The protein can be purified by four ions exchange chromatography steps and one gel filtration step.

The said proteins can also be obtained by the genetic engineering methods. For example, the sequence SEQ ID No1, possibly devoided of its C terminal part, can be cloned in an appropriate vector, and expressed in an expression system, such as the Pichia pastoris expression system, marketed by In Vitrogen.

In this system the sequence of the gene encoding the protein is cloned in an expression vector, and then linearized. Protoplasts from P. pastoris are transformed with the linearized vector.

The clones, in which a recombination occured leading to the replacement of the aOX1 sequence by the sequence of the gene of the protein that one seek to produce, are selected for their capacity to grow on an histidine deficient medium. The man skilled in the art can refer to the Manual of Methods for expression of recombinant proteins in Pichia pastoris, edited by In Vitrogen.

The protein, expressed by such a way, possibly secreted in the growth medium, is collected by the methods known by the man skilled in the art.

Such a protein can be used, in particular for the screening of molecules for their antifungal activity.

Thus an another subject of the present invention is a process for screening molecules for their anti fungal activity comprising the following steps:

bringing together the molecule to screen, and the protein or the protein fragment such as hereabove described, or encoded by a sequence such as hereabove described, and determining the effect of the molecule on the said protein.

The determination of the effect of the molecules on the said protein can be performed by measuring the $\beta$-(1–3) glucanosyltransferase (BGT2) activity. Such an activity can be determined by bringing together the said protein with a substrate on which it has an effect, which can be composed of laminarioligosaccharides comprising at least 10 glucosyl rests linked by $\beta$-(1–3) bonds. Indeed, when the protein is active, it cleaves a part of the molecule and links the obtained fragment on the non reducing end of an uncleaved substrate molecule.

The product, resulting from the protein activity is under the form of coupling products of the two laminorioligosaccharides. Such products can be detected by any method allowing the separation of oligosaccharides having different polymerization degrees, in particular by chromatography methods, such as high pressure liquid chromatography (HPLC) or thin layer chromatography (TLC). This last method, although less accurate than the first one, is the easiest method to be praticed.

In order to make use of such chromatography methods, the man skilled in the art can advantageously refers to the following manual: Carbohydrate analysis: a practical approach. Chaplin and Kennedy, 1986, IRC Press of Oxford.

This screening method allows to determine if the screened molecules possess an antifungal activity.

These molecules having antifungal activity show some effects towards the $\beta$-(1–3) glucanosyltransferase activity of said proteins. These effects can be for example inhibition of this activity.

The present invention is also related to molecules having an effect on said proteins, which can be screened by the process such described here above, as well as the use of these molecules for making a medicine, or for the treatment of diseases connected with the fungus, in vertebrates as well as in plants.

One of the advantages of the use of such molecules lies in the low frequency of occurrence of resistant fungus strains, contrary to the other known antifungal molecules.

The present invention is illustrated, without being limited by the following examples:

FIG. 1 illustrates the SDS-PAGE analysis of the purified 49 kDa protein: lane a, molecular weight standards; lane b, purified 49 kDa protein (1.5 μg); lane c, purified 49 kDa protein (1.5 μg) after treatment with N glycosidase F, lane d, N-glycosidase F only. The molecular weight of the protein bands and N-glycosidase F are indicated.

FIG. 2 represents the HPAEC analysis of products from the incubation of the 49 kDa enzyme with reduced laminarioligosaccharides. Purified 49 kDa protein was incubated with 8 mM of reduced laminarioligosaccharide of size $G_{11}$, $G_{12}$, $G_{13}$ or $G_{14}$ (reduced laminarioligosaccharides of respectively 11, 12, 13 or 14 residues of glucose) and the HPAEC profiles from samples taken at zero time and 15 min are shown, with the size of the major products indicated.

FIG. 3 represents the HPAEC analysis of products from the incubation of the 49 kDa enzyme with 8 mM of $rG_{16}$. The HPAEC profiles from samples taken at zero time, 30 min and 120 min are shown, with the size of the major products indicated.

FIG. 4 illustrates the transferase action and products formed from reduced laminarioligosaccharides.

FIG. 5 illustrates the effect of varying substrate concentrations. The 49 kDa transferase was incubated with 3 µM of [$^3$H]-$rG_{11}$ ($1\times10^6$ cpm) plus varying amounts of unlabeled $rG_{11}$. The % transfer was determined by comparing the proportion of label formed as $rG_6$ and $rG_{16}$. The inset shows the same data with the substrate concentration presented with a linear scale.

FIG. 6 illustrates the effect of pH on the rate of transfer. The 49 kDa transferase was incubated with 8 mM of [$^3$H]-$rG_{11}$ ($1\times10^6$ cpm). The reaction rates were determined by measuring the amount of label formed as $rG_{16}$ product. The buffers used were: ●, sodium citrate/citric acid; ○, imidazole/citric acid; X, sodium acetate/acetic acid; ■, Tris/glycine, ▲, phosphate/NaOH; □, Tris/acetic acid; Δ, glycine/HCl.

FIG. 7 represent the sequence from the BGT2 gene of *A. fumigatus* (A) compared to PHR1 and GAS1 isolated from *C. albicans* (C) and *S. cerevisiae* (S). The aminoacid underlined correspond to the supposed intron.

Figure 9:
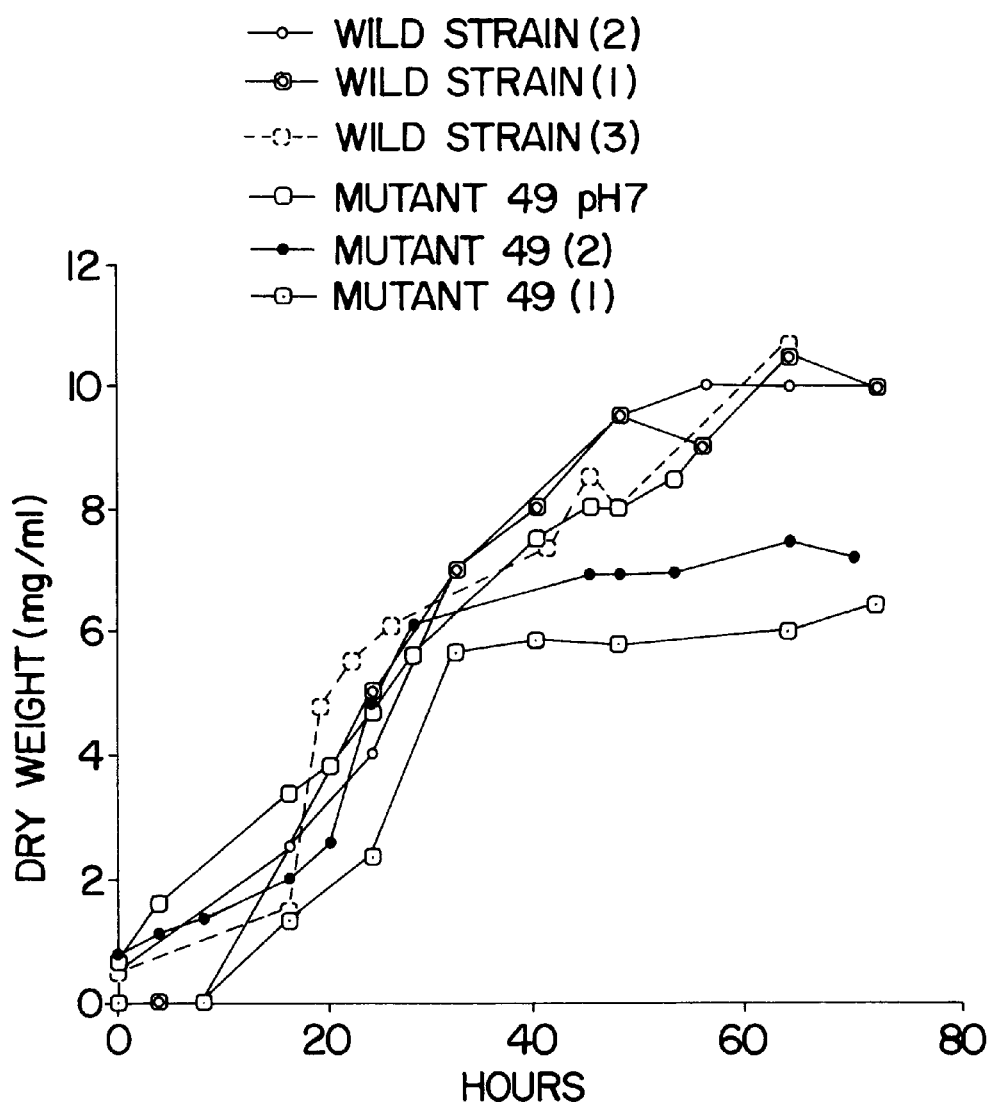

FIG. 9 illustrates the cinetic growth of the mutant 49 compared to the wild strain. For each strains, several experiences were done (this is indicated by the number 1, 2, 3). The legend mutant 49 pH7 correspond to the cinetic growth of the mutant 49 at regulated pH7 of the growth medium.

Figure 10:
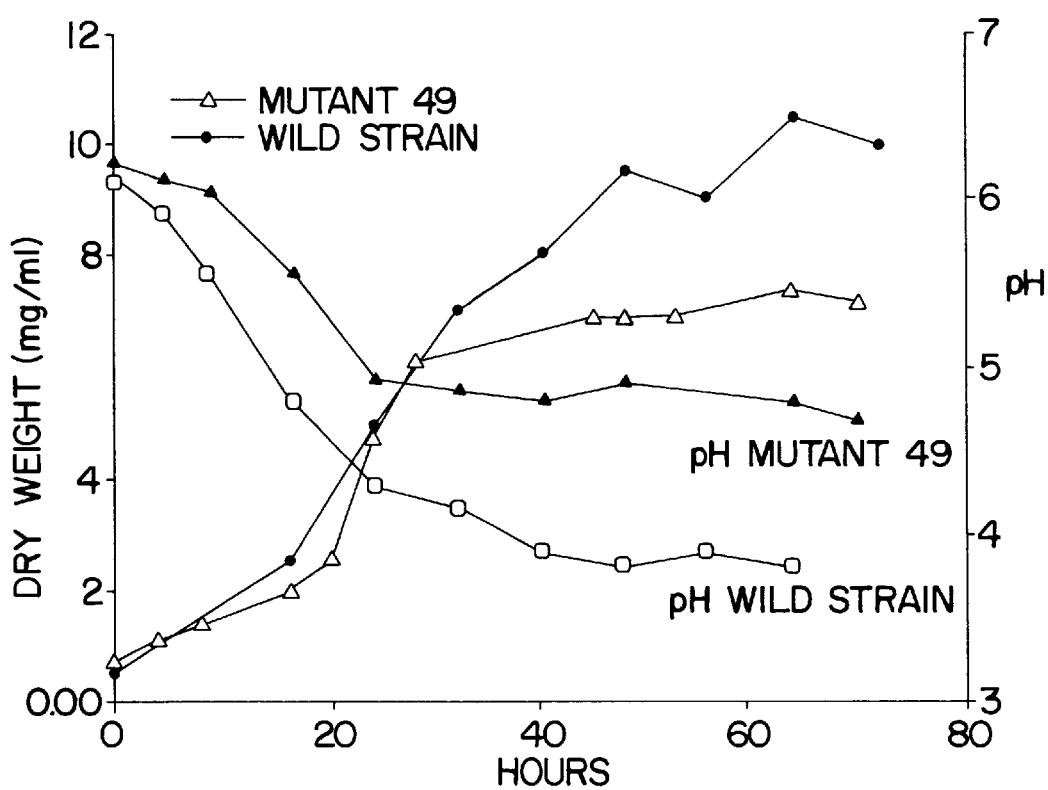

FIGS. 10 illustrates the growth of the wild strain and of the mutant Δ49 compared to the pH of the growth medium.

Figure 11:
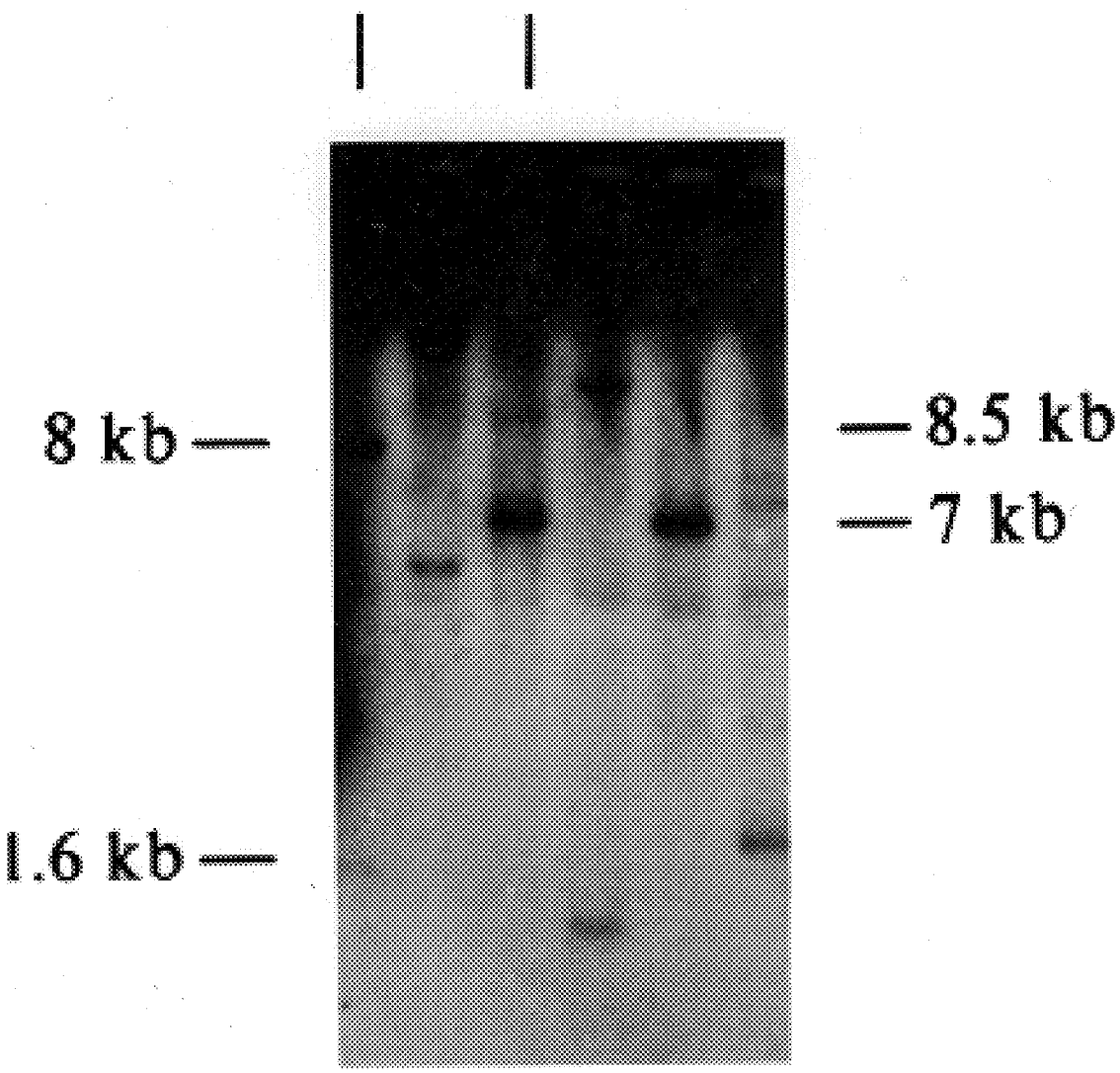

FIG. 11 is a Southern blot of *A. fumigatus* DNA digested with HindIII and BamH1 hybridized at low stringency with the BGT2 gene as probe. There is no restriction site HindIII and BamH1 in DNA corresponding to the BGT2 gene. The two bands observed for each digestion are in agreement with the existence of an homolog of BGT2 in *A. fumigatus* genomic DNA.

EXAMPLES

Experimental Procedures

1. Preparation of cell walls and autolysis

*A. fumigatus* CBS 144–89 (available at the Collection Centralbureau voor Schimmelculture) was grown in a 15 L fermenter in 2% glucose, 1% mycopeptone (Biokar Diagnostics) plus 0.1% silicone antifoam 426R (Rhodorsil) at 25° C. (500 rpm agitation, 0.5 vol.vol$^{-1}$.min$^{-1}$ aeration) for 42h. A culture grown for 3 days in a 2 L fermenter under the same conditions was used as inoculum (8% (v/v)). The mycelia were collected by filtration under vacuum and broken by passing through a Dyno-mill in the presence of glass beads (W. A. Bachofen AG, Basel, Switzerland) (0.5–0.75 mm diameter). The progress of cell disruption was followed by microscopic examination. The broken mycelial suspension was centrifuged (8,000 g, 15 min) and the cell wall pellet washed 3 times with water and once in 50 mM Na acetate, pH 5.6 containing 5 mM Na azide before being resuspended in the same buffer (250 g wet weight per L of buffer) and incubated (200 rpm agitation) at 37° C. After 72 h the suspension was centrifuged (10,000 g, 15 min) and the supernatant was placed in dialysis tubing, concentrated 5–10 fold with polyethyleneglycol 20,000, dialysed against 5 mM Na acetate, pH 5.6, recentrifuged (10,000 g, 15 min) and filtered (0.45 µm filter). This preparation is referred to as the autolysate.

2. Enzyme purification

Fractions collected during every chromatography step were assayed for enzyme activity using the non-radioactive transferase assay (see below). The concentrated, dialysed autolysate was applied to a column (4×18 cm) of DEAE-Sepharose Fast-Flow (Pharmacia) equilibrated in 5 mM Na acetate, pH 5.6 and eluted with a linear gradient of 0–1M NaCl (2,000 ml) at a flow rate of 240 ml h$^{-1}$. Fractions containing the transferase activity were pooled, dialysed against 10 mM β-mercaptoethanol, 5 mM EDTA, 10 mM Na acetate buffer, pH 4.0 and applied to a Mono S column (HR 5/5, Pharmacia) and eluted with a linear NaCl gradient (0–300 mM in 40 min) at a flow rate of 0.8 ml min$^{-1}$. The fraction containing the transferase activity were pooled, dialysed against 10 mM Tris/HCl, pH 7.0 and deposited on a DEAE-5PW column (8×75 mm, TosoHaas) and eluted with a linear NaCl gradient (0–300 mM in 60 min) with a flow rate of 0.75 ml min$^{-1}$. Fractions containing the transferase activity were pooled, dialysed against 10 mM β-mercaptoethanol, 5 mM EDTA, 10 mM Na acetate, pH 4.0 and deposited on a CM-5PW column (8×75 mm, TosoHaas) and eluted with a linear NaCl gradient (0–300 mM in 60 min) at a flow rate of 0.8 ml min$^1$. Transferase containing fractions were pooled and concentrated by speedvac and fractionated on a superdex HR75 column (Pharmacia) equilibrated in 10 mM Tris/HCl, pH 7.0 containing 150 mM NaCl, at a low rate of 0.75 ml min$^{-1}$. Fractions containing the purified transferase were pooled, dialysed against 5 mM Na citrate, pH 5.0, concentrated by speedvac and stored at −20° C. until used.

3. Transferase assays

Enzyme fractions were assayed for the presence of transferase activity by incubating in 50 mM Na citrate, pH 5.0 at 37° C. (10 µl assay volume) with a borohydride-reduced laminarioligosaccharide (8 mM final) of at least $G_{10}$ in size. Samples (3 µl) were taken at different times and added to ice cold 50 mM NaOH (47 µl) to terminate the reaction and frozen until analysed by high performance anion exchange chromatography (HPAEC). Because of variations in peak intensities from day to day with Pulsed Electrochemical Detector (PED) detection, transferase activity was quantitated using [$^3$H]-reduced laminarioligosaccharides as substrates and measuring the appearance of label in the products after separation by HPAEC, using an on-line Radiomatic flow scintillation analyzed 150TR (Packard). Unless stated otherwise, assays for enzyme characterization studies were performed as above with 0.25 µg of purified transferase.

4. Colorimetric assays

β-Glucanase activity in protein fractions was measured by a reducing sugar assay using the p-hydroxybenzoic acid hydrazide reagent with borohydride-reduced laminarin instead of carboxymethyl pachyman as substrate (Ram et al, 1988, Life sci Adv., 7, 379–383). Exo-β-glucanase/β-glucosidase activities were measured by incubation of enzyme fractions with p-nitrophenyl-β-D-glucopyranoside (Hartland et al, 1991, Proc. R. Soc. London B, 246, 155–160). Protein was estimated using the BioRad protein assay according to the manufacterer's instructions, with bovine serum albumin as standard.

5. High performance anionic exchange chromatography

Carbohydrate samples from transferase assays were analysed on a CarboPac PA1 (4×250 mm) Dionex analytical column (with a PA1 guard column) on a Dionex HPAEC system with pulsed electrochemical detection (PED-2 cell), fitted with a combination pH Ag/AgCl reference electrode and using a potential of 0.4 V for the first 0.5 sec of detection. Oligosaccharides were eluted with the following conditions: flow rate of 1 ml/min, buffer A 50 mM NaOH; buffer B: 500 mM sodium acetate in 50 mM NaOH; gradient: 0 to 2 min, 98% A 2% B (isocratic), 2 to 15 min 75% A 25% B (linear), 15 to 45 min 60% A 40% B (linear).

Laminarioligosaccharide standards were obtained from Seikagaku (Japan).

6. Thin layer chromatography (TLC)

Laminarioligosaccharides were visualised by thin-layer chromatography on silica-gel 60 (Kieselgel, Merck) using n-butanol/acetic acid/water; (2/1/1.5) as eluent and orcinol sulphuric staining.

Degree of polymerization (dp) of oligosaccharides were also determined by HPAE chromatography using a pulsed electrochemical detector and an anion-exchange column (Carbo5PAC PA1, 4.6×250 mm, Dionex).

7. Preparation of reduced substrates

Laminarioligosaccharides were obtained by a partial acid hydrolysis (6.5M TFA, 15 min. 100° C., followed by 1M TFA, 45 min, 100° C.) of curdlan (Serva). TFA was removed by rotary evaporation in the presence of methanol. Oligosaccharides were reduced overnight with $NaBH_4$ (1:0.5 (w/w) in 0.1M NaOH at room temperature). Reducing and [$^3$H]-labelled laminarioligosaccharides were similarly prepared by reduction with $NaB^3H_4$ (Amersham, 10–20 Ci/mmol, 10 mCi per mg oligosaccharide) overnight followed by further reduction with $NaBH_4$ as before. Excess $NaBH_4$ was destroyed by the addition of acetic acid to pH 5–6, and borate salts were removed by rotary evaporation in the presence of methanol. The reduced oligosaccharides were desalted by gel filtration on a Sephadex G15 column (1.2×80 cm, 8 ml h$^{-1}$, equilibrated in water) and collected after detection by the orcinol-sulphuric acid method (Ashwell, 1966, Methods Enzymol, 8, 85–95). The laminarioligosaccharides were separated by HPAEC on a CarboPac PA1 (9×250 mm) preparative column (Dionex) with a 15–350 mM Na acetate gradient in 50 mM NaOH (45 min) at a flow rate of 4 ml min$^{-1}$. Collected oligosaccharide fractions were neutralised by acetic acid, desalted by gel filtration on a Sephadex G15 column as before and freeze dried. Laminarin (Sigma) was similarly reduced, but desalted by dialysis against 0.5% acetic acid, followed by dialysis against water, and then freeze-dried. Gentiooligosaccharides were prepared as above (without reduction) from pustulan (Calbiochem) which has been finely ground by mortar and pestle. Maltoheptaose and cellopentaose were from Boehringer Mannheim and Sigma, respectively. Chitohexaose was a generous gift from Dr. A. Domard (Université Claude Bernard, Villeurbanne, France). Borohydride-reduced $G_{10}$ containing an intrachain β-(1–6)-linkage at the 6th linkage from the reducing end ($rG_{10}$*) was obtained by incubating reduced laminarihexaose ($rG_6$) with an enzyme homologue to Candida BGT1 purified from A. fumigatus. The $rG_{10}$* transferase product was separated and purified as for the laminarioligosaccharides above.

7. SDS-polyacrylamide gel electrophoresis

Protein samples were analysed by SDS-PAGE (Laemmli, 1970, Nature, 227, 680–685) using 10% separating gels and 4% stacking gels. Proteins bands were visualised by staining with Coomassie Blue. De-N-glycosylation of glycoprotein was done using recombinant N-glycosidase F(Oxford GlycoSystems) according to the manufacture's instructions.

8. $^1$H-NMR Spectroscopy

Two samples were analysed: a reduced $G_{10}$ laminarioligosaccharide used as a standard and a reduced $G_{15}$ oligosaccharide which was obtained after incubation of $rG_{10}$ with the transferase and purified by HPAEC. Dry samples were deuterium exchanged by freeze drying and dissolving in $D_2O$ (99.95%, Solvents Documentation Synthese, France). Spectra were recorded at 300K and 318K on a Varian Unity 500 spectrometer operating at a proton frequency of 500 Mhz. The OH resonance of residual water was suppressed by selective irradiation during the relaxation delay. No 3-trimethylsilyl propionic acid was used as an external reference.

EXAMPLE 1

Purification of the 49 kDa protein

In order to study cell wall-associated β-glucanosyl transferase activities in A. fumigatus, a high performance anion-exchange chromatography (HPAEC) assay was developed using borohydride-reduced laminarioligosaccharides as substrates. A novel β-(1–3)-glucanosyl transferase (BGT2) activity was detected in semi-purified fractions from a cell wall autolysate of A. fumigatus, which remained associated with a protein of 49 kDa throughout its purification.

The protein was purified to apparent homogeneity by four conventional ion-exchange chromatography steps and a gel filtration step.

Figure 1:
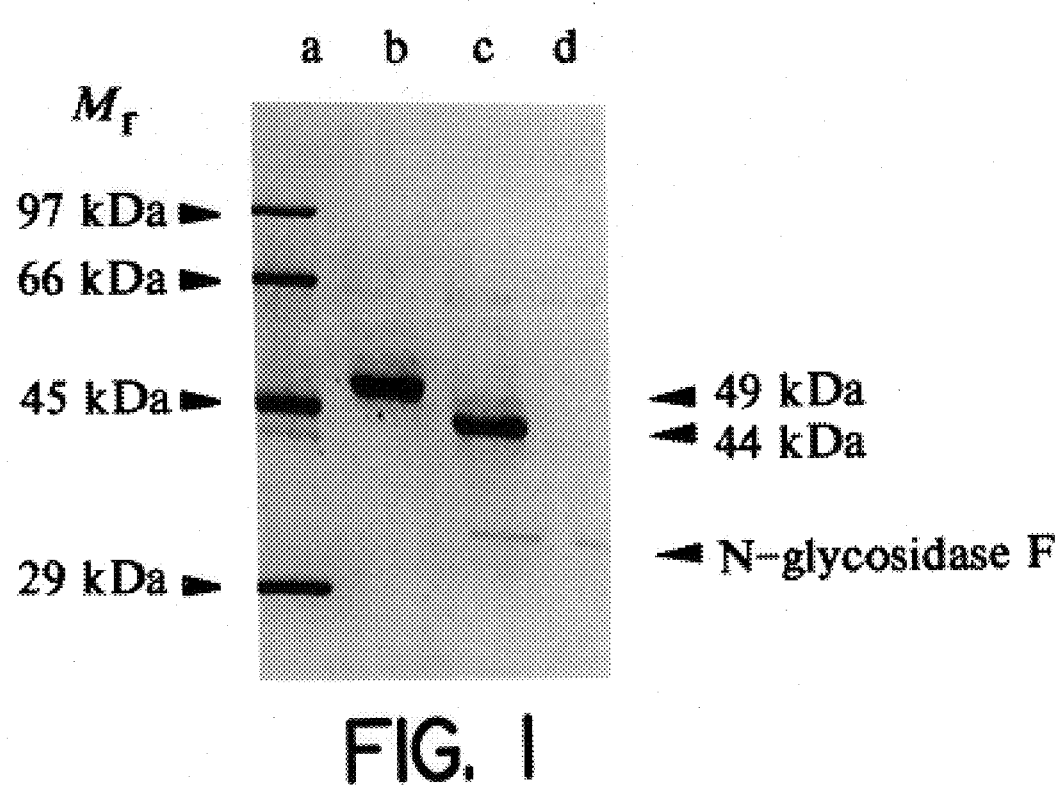
Figure 2A:
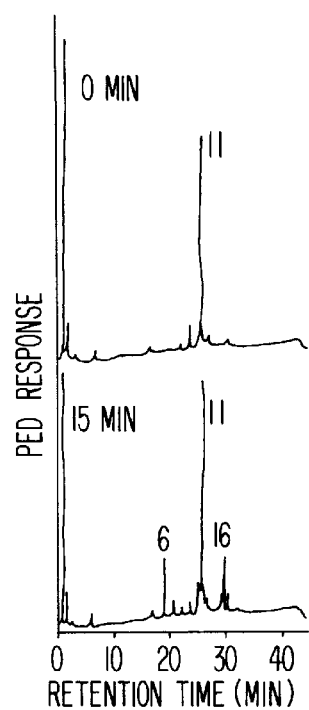
Figure 2B:
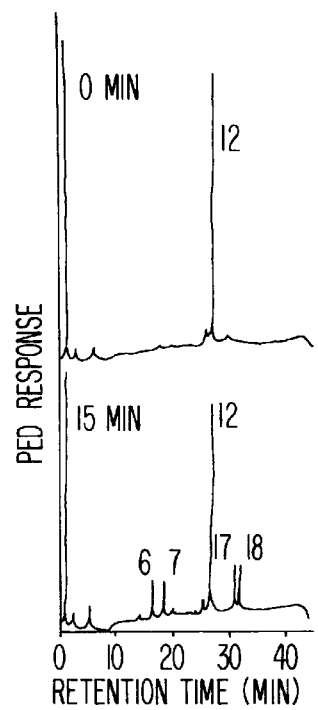
Figure 2C:
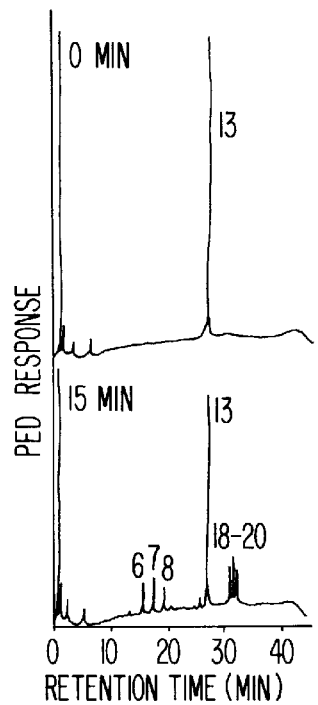
Figure 2D:
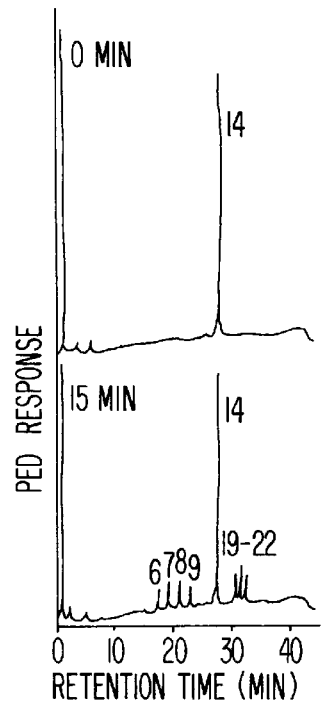

The transferase activity was clearly detectable only after the second chromatography step (Mono S). SDS-PAGE analysis of the purified fraction showed one major band at 49 kDa (FIG. 1 well b). To determine whether it contained N-linked carbohydrate the protein was digested with N-glycosidase F. The digested protein ran on SDS-PAGE as a 44 kDa protein (FIG. 1, well c), indicating that is contained about 5 kDa of N-linked carbohydrate.

EXAMPLE 2

Enzyme activity of the 49 kDa protein

Analysis by HPAEC of the products resulting from the incubation of the 49 kDa protein with a borohydride-reduced laminarioligosaccharide ($rG_n$) of size $G_{10}$ or greater allowed the characterization of a novel glucanosyl transferase activity.

The major initial products from the incubation with $rG_{11}$ were $rG_6$ and $rG_{16}$; $rG_{12}$ gave $rG_6+rG_7$ and $rG_{17}+rG_{18}$; $rG_{13}$ gave $rG_6$ to $rG_5$ and $rG_{18}$ to $rG_{20}$; and $rG_{14}$ resulted in the formation of $rG_6$ to $rG_9$ and $rG_{12}$ to $rG_{22}$ (FIG. 2). Importantly, there were no non-reduced laminarioligosaccharide products detected, confirming the absence of any ondo-β-(1–3)-glucanase activity. The presence of such an activity would have resulted in the formation of a mixture of reduced and non-reduced hydrolysis products, the latter having quite different retention times. In addition, there was no glucose detected, and together with the absence of both p-nitrophenyl β-glucopyranoside hydrolysis and net reducing sugar formation from borohydride reduced laminarin in the corresponding colorimetric assays, confirmed the absence of exo-β-(1–3)-glucanase and β-glucosidase activity.

The pattern of products obtained (FIG. 2) is consistent with an endo-type glucanosyl transferase activity in which the glucan chain is cleaved in an endolytic fashion, releasing the reducing-end portion, and the remainder is transferred to another glucan chain, forming a larger transferase product. Thus, in the simplest reaction with $rG_{11}$, the enzyme cleaves the substrate releasing $rG_6$ from the reducing end of the substrate molecule, and the remaining $G_5$ is then transferred to another $rG_{11}$ molecule acting as an acceptor, to form the $rG_{16}$ transferase product:

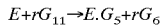

$E+rG_{11} \rightarrow E.G_5+rG_6$

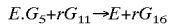

$E.G_5+rG_{11} \rightarrow E+rG_{16}$ where E represents the enzyme. The transferase cleaves $rG_{12}$ in two different ways resulting in two different transferase products:

| Transferase reaction | Rate of transfer (nmol.min$^1$ .mg protein$^{-1}$) |
| --- | --- |
| $rG_{11} + [^3H] - rG_5 \rightarrow RG_6 + [^3H] - rG_{10}$ | 203 |
| $rG_{11} + [^3H] - rG_6 \rightarrow RG_6 + [^3H] - rG_{11}$ | 387 |
| $rG_{11} + [^3H] - rG_7 \rightarrow RG_6 + [^3H] - rG_{12}$ | 484 |
| $rG_{11} + [^3H] - rG_8 \rightarrow RG_6 + [^3H] - rG_{13}$ | 586 |

Similarly, with $rG_{13}$ and $rG_{14}$ the transferase cleaves in three and four different ways, respectively, each time transferring the non-reducing end portion to another $rG_{13}$ or $rG_{14}$ acceptor molecule.

Further analyses of incubations of the 49 kDa transferase with smaller, reduced laminarioligosaccharides showed that the reaction with $rG_{10}$ gave $rG_5+rG_6$ and $rG_{14}+rG_{15}$ as the major initial products, whereas the reaction with $rG_9$ was extremely slow, forming small peaks at $rG_5$ to $rG_8$ and $rG_{10}$ to $rG_{13}$. There were no products detected upon incubation with reduced laminarioligosaccharides of size $G_8$ and smaller.

To determine the enzyme's relative rate of reaction with varying sized laminarioligosaccharides, the 49 kDa enzyme (0.25 μg) was incubated separately with 8 mM of [$^3$H]-labeled $rG_{10}$ to $rG_{15}$ and the rate of formation of labeled products was measured. The rate with $rG_{10}$ (328 nmol.min$^{-1}$) was approximately 50% of that of the larger substrates and there appeared to be no significant difference between the reaction rates for $rG_{11}$ to $rG_{15}$ (648±16 nmol.min$^{-1}$ mg protein$^1$).

Analysis of extended incubations of purified enzyme with a reduced laminarioligosaccharide of at least $G_{10}$ in size showed that the initial transferase products can be re-used subsequently either as donors or as acceptors, resulting in the formation of products of increasing size, until they drop out of solution because of their insolubility in aqueous buffer. A 30 min. incubation with $rG_{16}$ (containing some contaminating $rG_{15}$) resulted in the formation of reduced, major initial products of sizes $G_6$ to $G_{11}$ and $G_{21}$ to $G_{26}$ (FIG. 3), but after 120 min larger transferase products had appeared of up to at least $G_{20}$ in size (FIG. 3). The products of $G_{29}$ in size and larger had precipitated in the bottom of the incubation tube as these were missing when the reaction mixture was briefly centrifuged and the supernatant was analyzed. Incubation of purified enzyme with reduced laminarin resulted in the production of smaller and larger products, indicating that soluble oligosaccharides of $G_{30}$ in size and larger could act both as donor and acceptors in the reaction.

To determine the smallest laminarioligosaccharide which could act as an acceptor, the purified transferase was incubated with 4 mM or $rG_{11}$ as the donor plus 16 mM of $rG_8$ or smaller as an acceptor. Analyses of the incubations containing $rG_{11}$ plus $rG_4$ or smaller showed the formation of $rG_6$ and $rG_{16}$ as the only major initial products, indicating that only $rG_{11}$ was being used as an acceptor. However, incubations containing $rG_{11}$ plus $rG_5$ to $rG_8$ showed additional transferase products consistent with the latter oligosaccharides being used as acceptors. For example, the reaction of $rG_{11}$ plus $rG_2$ resulted in the initial formation of $rG_6$, $rG_{12}$ and $rG_{16}$ consistent with:

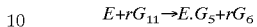

$E+rG_{11} \rightarrow E.G_5+rG_6$

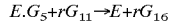

$E.G_5+rG_{11} \rightarrow E+rG_{16}$

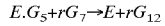

$E.G_5+rG_7 \rightarrow E+rG_{12}$

Figure 4:
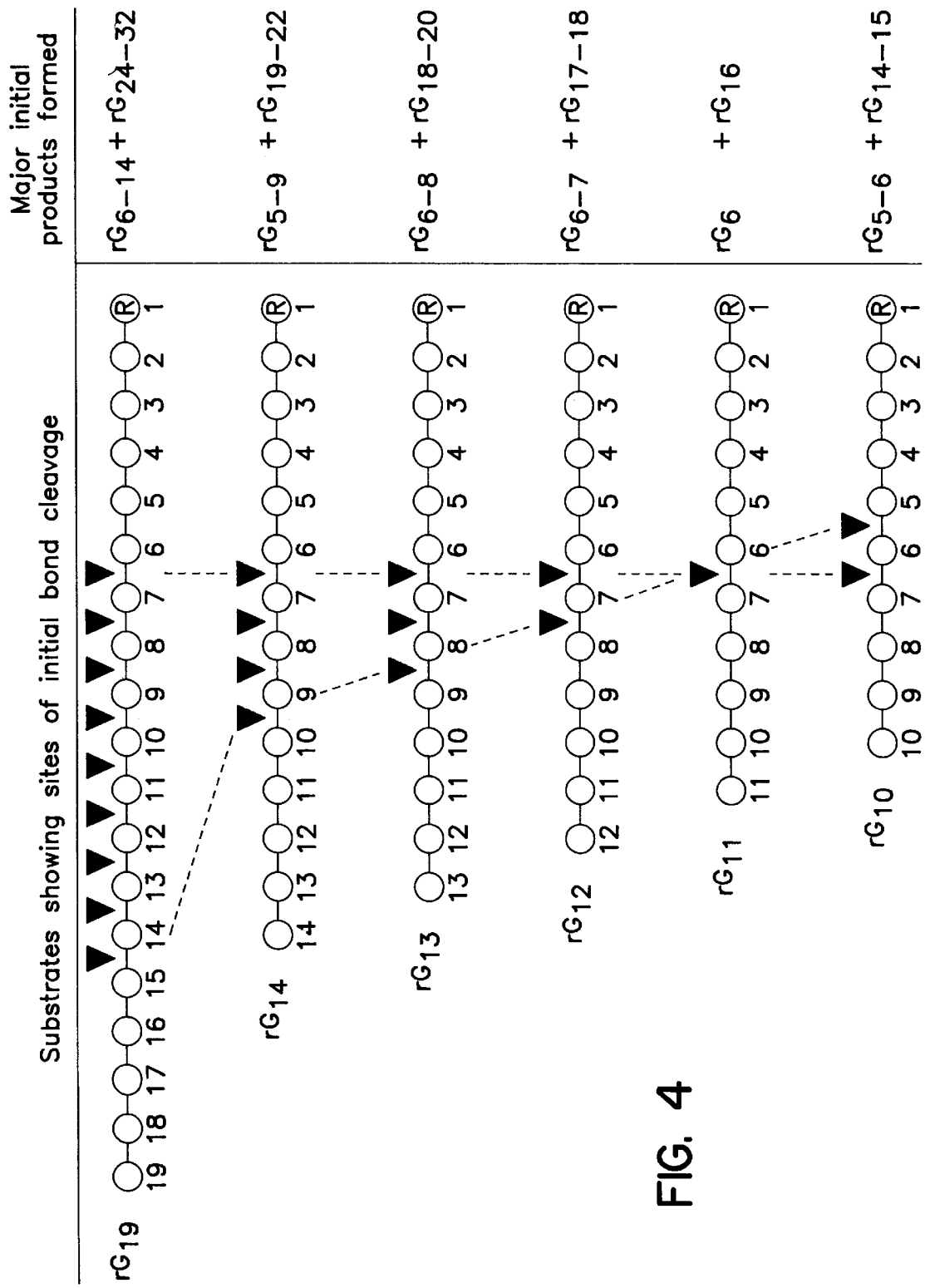

The relative rate of the reaction with these acceptors was determined by using 2 mM of $rG_{11}$ as the donor plus 32 mM of [$^3$H]-reduced acceptor and measuring the formation of labelled transferase product (FIG. 4). Under these conditions the reaction with $rG_{11}$ being used as an acceptor is negligible. The reaction rate increased with increasing chain length, indicating that the 40 kDa enzyme prefers larger laminarioligosaccharide acceptors.

The transferase showed no activity towards gentiooligosaccharides ($G_{3-8}$ in size), chitohexaose, cellopentaose or maltoheptaose neither in the presence or absence of $rG_{11}$, suggesting the enzyme uses exclusively β-(1–3) glucan as a donor was shown by using a kinked reduced $G_{10}$ ($rG_{10}^*$) similar to laminaridecaose, except that the 6th linkage from the reducing end is a β-(1–6)-linkage. Incubation of the 49 kDa enzyme with 8 mM of $rG_{10}^*$ gave no products indicating that it was not a donor. However, a similar incubation in the presence of 2 mM $rG_{22}$ resulted in the formation of $rG_6$ and a peak eluting at the position of $rG_{15}$ as the major initial products, showing that $rG_{10}^*$ could act as an acceptor.

EXAMPLE 3

$^1$H-NMR analysis of the reduced $G_{16}$ transferase product

To determine whether the 49 kDa transferase produced a new linkage type during transfer, the $rG_{16}$ transferase product was purified from an incubation of the transferase with $rG_{11}$. Approximately 300 μg of the product was analyzed by $^1$H-NMR. The 1D spectrum of the $rG_{16}$ transferase product presented 3 chemical shifts in the anomeric region:

δ=4.60 ppm corresponding to the glucose residue linked to the glucitol group;

δ=4.75 ppm corresponding to the glucose residue of the non-reducing end;

δ=4.80 ppm corresponding to the intrachain glucose residues linked in β-(1–3).

The relative intensity of the anomeric signals indicated 1,1 and 13 protons respectively. Since glucitol does not give any signal in the anomeric region, it confirmed the length of the oligosaccharide (16 residues). Coupling constants measured on these signals were in agreement with β-linked glucose residues ($^3J_{1,2}$=7,9 Hz). The presence of a single glucose unit at the non-reducing end indicated that the 49 kDa protein transferred onto the non-reducing end of the β(1–3) glucan acceptor.

The 1D spectrum of the $rG_{16}$ product was identical, except for the relative intensity of the 4.80 ppm signal to that of a $rG_{10}$ laminarioligosaccharide standard. In addition, no chemical shift characteristics of glucose residue linked in (1–2), (1–4), or (1–6) were seen confirming that the $rG_{16}$ was a laminari-hexadecaose. The co-elution of the $rG_{16}$ product with a $rG_{16}$ reference on HPAEC and the insolubility of the larger product were consistent with the production of a β-(1–3) linkage during transfer.

EXAMPLE 4

Effect of substrate concentration on the reaction products

To determine whether lowering the acceptor concentration would promote hydrolysis reactions, the 49 kDa transferase was incubated with 3 μM of [$^3$H]-rG$_{11}$ plus decreasing amounts of unlabelled rG$_{11}$. There was an observed shift from (i) transfer to (ii) hydrolysis (FIG. 5, insert):

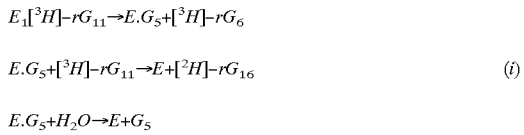

$$E.G_5 + H_2O \to E + G_5$$

Figure 5A:
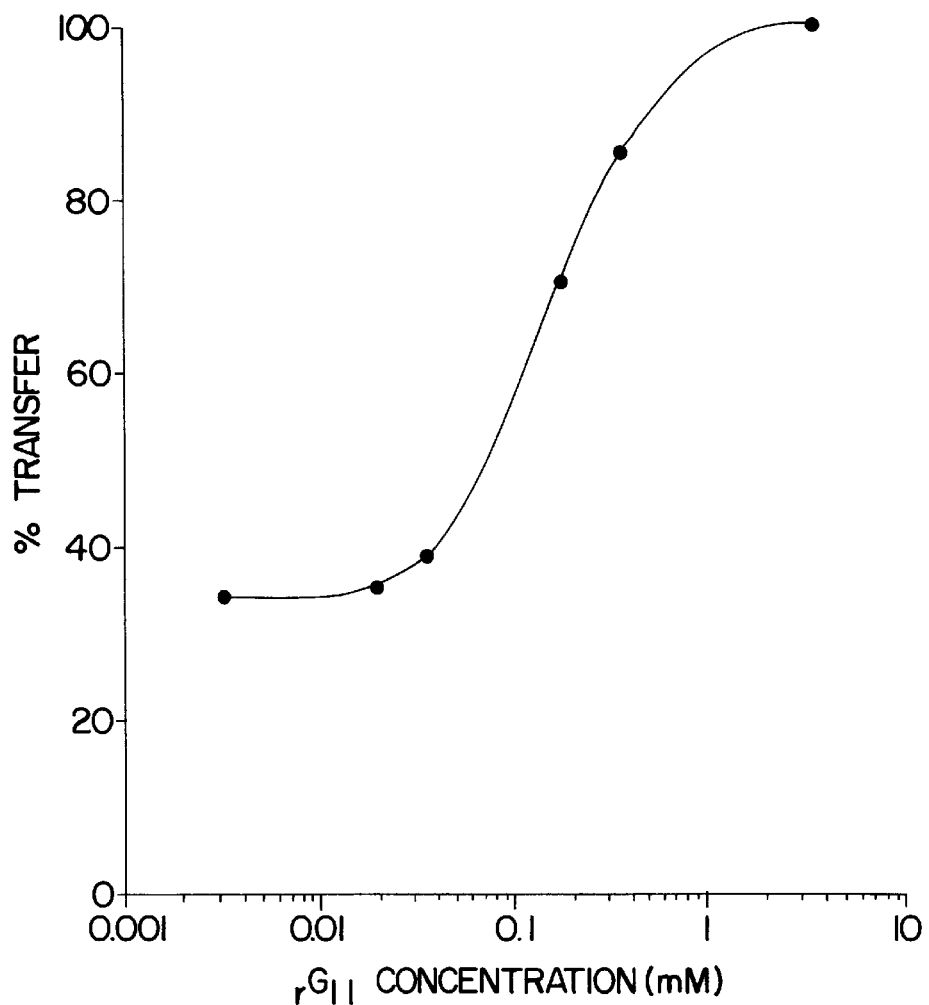
Figure 5B:
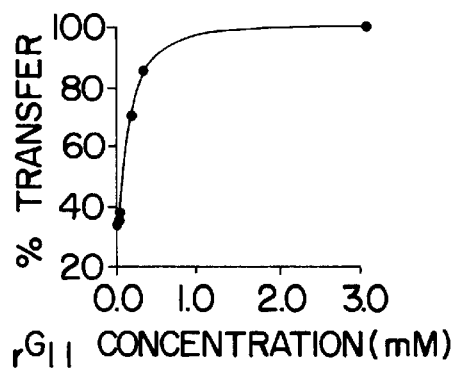

The percentage of transfer was determined by measuring the formation of labelled rG$_{16}$ (transfer only) compared to that of labelled rG$_6$ (transfer plus hydrolysis) in the reaction. At 3 mM rG$_{11}$, only transfer was detected. As the substrate concentration decreased to 18 μM, the percentage of transfer levelled out to about 35% and did not decrease significantly with a lower substrate concentration (3 μM) (FIG. 5). Decreasing the buffer concentration to 10 mM did not alter the percentage of transfer at any of the substrate concentrations. It appears that under the given conditions the 49 kDa transferase was unable to catalyze more than about 65% hydrolysis by simply reducing the substrate concentration to very low levels.

EXAMPLE 5 pH optimum and stability

Figure 6:
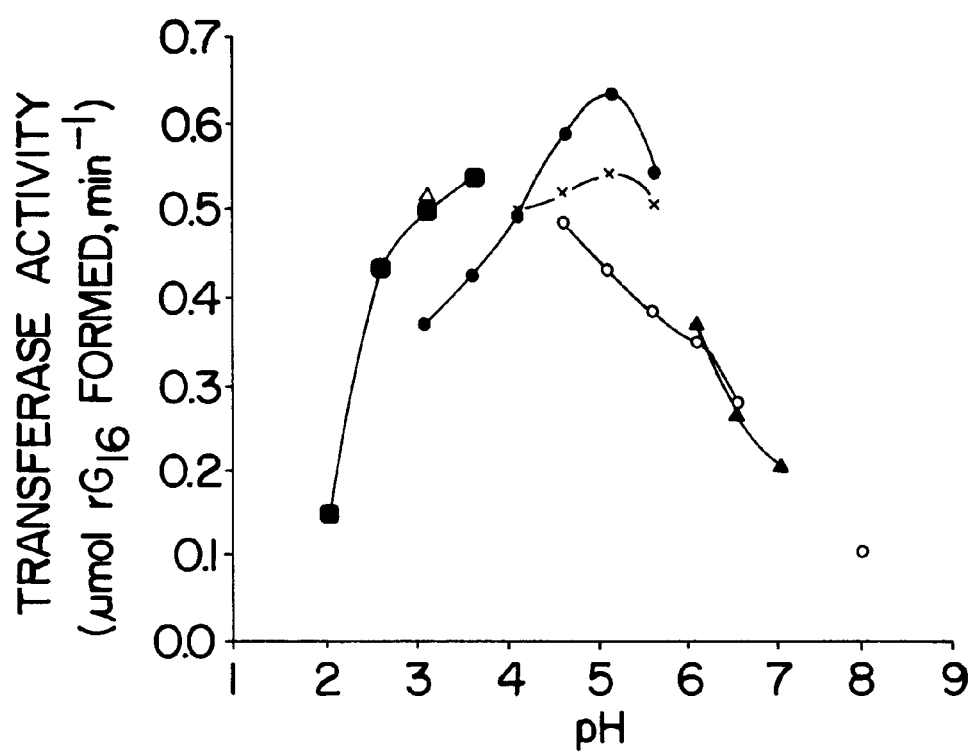

The 49 kDa enzyme was assayed at different pH values, checked for stability upon storage and the N-glycosylated enzyme assayed for activity. The enzyme was active over a broad range of acidic pH, showing activity of more than 50% of maximum between pH 2.5 and 6.0. The enzyme displayed a pH optimum of about 5.0 in citrate buffer (FIG. 6). The enzyme was very stable and could be kept at 4° C. in 10 mM citrate buffer, pH 5.0 for many weeks, or dried by speed-vac and later resuspended in buffer, or stored at −20° C. without significant loss of activity. The de-N-glycosylated 44 kDa enzyme prepared under non-denaturing conditions was as active as the natived, glycosylated enzyme when incubated with 8 mM rG$_{11}$.

EXAMPLE 6

Kinetic analysis

The 49 kDa enzyme catalyzes its transferase reaction via a bi-reactant (two-step) mechanism with initial hydrolysis of the substrate to release the reducing-end portion, and subsequent transfer of the remainder to the non-reducing end of a substrate molecule playing the role of acceptor molecule.

Using rG$_{11}$ as the substrate, it was impossible to calculate an apparent K$_m$ accounting for both reaction steps. To determine a K$_m$ for the donor site, we used an acceptor which was not a donor. [$^3$H]-rG$_7$(1×10$^6$ cpm) was used as the acceptor at high concentration (64 mM) with varying concentrations of rG$_{11}$ kept below 8 mM. Under these conditions the reaction proceeded with rG$_{11}$ as the donor and rG$_7$ being used in favour of rG$_{11}$ as the acceptor, as determined by the absence of formation of the rG$_{16}$ transferase product. The initial rate of the reaction was determined by measuring the appearance of labelled rG$_{12}$.

An apparent K$_m$ of 5.3 mM was obtained from the double-reciprocal plot (r$^2$ value=0.997).

EXAMPLE 7

Cloning, sequencing and disruption of the gene encoding for BGT2 in *A. fumigatus*

Two aminoacid sequences have been obtained from the purified BGT2 protein. The NH$_2$ terminal sequence was DVTPITVKGNAFFKGDERFY and an internal sequence was DAPNWDVDNDALP.

A 38 mer oligonucleotide designed on the N-terminal having the following sequence SEQ ID NO4:

(AAF GG(T/C) AA(C/T) GC(T/C) TTC TT (C/T) AAG GG(T/C) GA (T/C) GAG CG(T/C) TTC TA) was used to screen a genomic library constructed in EMBL3 phage after Sau3A partial digestion of *A. fumigatus* DNA as described by Monod (1994, 33–40. Mol. Biology of pathogenic fungi, B. Maresca and G. S. Kobayashi).

Transfer is performed on Zetaprobe membranes. Prehybridization and hybridization of the membrane was at 50° C. in a solution containing 5 x SSC, 20 mM Na$_2$HPO$_4$, pH 7, SDS 7%, 10X Denhardt and 1% salmon sperm. Washing of the membrane was done at 42° C. twice in a solution containing 3XSSC, 10X denhardt, 5% SDS, 25 mM Na$_2$HPO$_4$ and twice in a 1XSSC, 1% SDS solution.

Cloning and sequencing of the gene coding for BGT2 showed significant homologies with the PHR1 and GAS1 genes previously identified in *C. albicans* and *S. cerevisiae* respectively (Saporito Irwin et al. (1995) Mol Cell Biol., 15, 601–613) (Nuoffer et al. (1991) Mol Cell Biol, 11, 27–37) (Gatti et al, J. Biol. Chem., (1991), 266, 19, 12242–12248) (FIG. 7).

Disruption of the BGT2 gene was performed using the vector pAN7-1 (Punt et al. (1987) Gene 56, 117–124) provided by P. Punt (TNO, Rijisnik). This vector has been modified as pN4 by (Paris et al. (1993) FEMS Microbiol. lett. 111, 31–36) by the replacement of a HindIII restriction site by a Sma1 site. Around 50% of the BGT2 ORF has been replaced by pN4 at a EcoRV restriction site. Integrative transformation was done as described previously (Paris, (1994) Isolation of protease negative mutants of *Aspergillus fumigatus* by insertion of a disrupted gene, p. 49–55. Mol. Biology of pathogenic fungi, Maresca and G. S. Kobayashi) using Novozyme produced protoplasts and the linearized plasmid in presence of PEG.

The Δ49 mutant of *A. fumigatus* obtained has been deposited on Jul. 30, 1996 to the CNCM under the deposit number I 1764.

Figure 8:
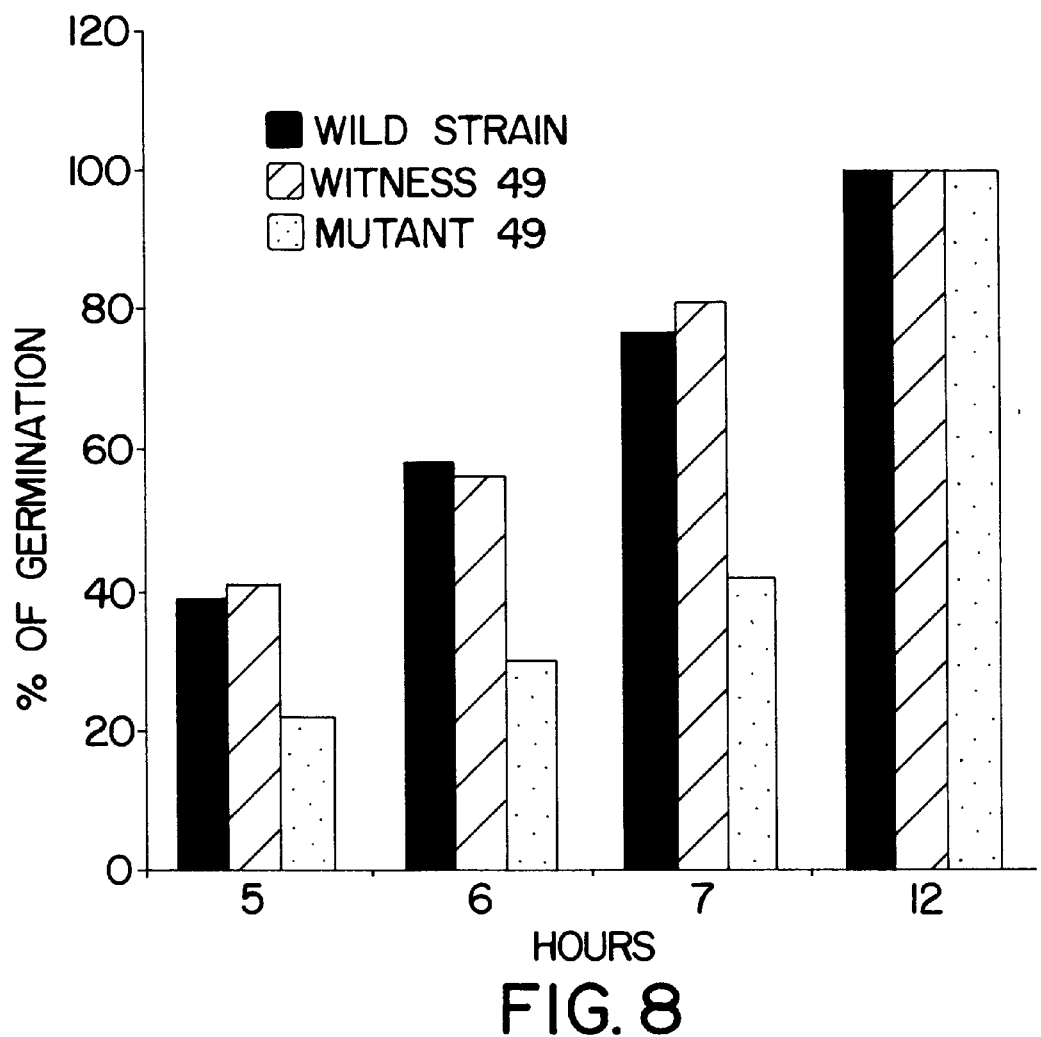
FIG. 8 illustrates the percentage of germination from wild strain, witness 49 (a strain transformed by the disrupted gene BGT2, but in which the BGT2 gene was not replaced by the disrupted gene in the genomic DNA) and mutant Δ49.

It does not show any distinct phenotype from the wild strain with two noticeable exceptions.

a delay in conidial germination (FIG. 8).

a total growth inhibition when the pH of the culture medium drops below 5 (FIGS. 9 and 10).

An homolog of the BGT2 gene has been identified in *A. fumigatus* using the BGT2 gene as a probe to screen Southern blots of *A. fumigatus* DNA digested by HindIII and BamH1 (FIG. 11). Transfer is performed on Genescreen membranes. Prehybridization and hybridization of the membrane was at 42° C. in a solution containing 5XSSC, 20% formamide, SDS 1%, 10X Denhardt sulfate and 1% salmon sperm. Washing of the membrane was done at 42° C. twice in a solution containing 3XSSC, 1% SDS.

EXAMPLE 8

Cloning and sequencing of BGT2 cDNA

The BGT2 cDNa has been obtained by amplication with two primers P1 adnc (SEQ ID NO5) 5'(GAATTCGACGACGTTACTCCCATCACT 3' and P2 (SEQ ID No:6) 5'TCTAGAGGGTATGAGAAGAA-CAAATCA 3' from 10 ng of cDNA, 1U of Taq polymerase, 200 mM of each of the primers. 30 amplication cycles, composed of one minute at 95° C., one minute at 55° C. and one minute at 72° C. were performed.

The amplifying preparation has been then cloned in a vector with the help of TA cloning kit (In Vitrogen).

EXAMPLE 9

Expression of the β(1–3) glucanosyltransferase

Experiments using Triton X114 partition with or without GPI-Phospholipase C treatment showed that BGT2 of *A. fumigatus* is anchored by a GPI residue in the plasma membrane.

Anchoring of the protein to the membrane is not necessary to conserve the enzyme activity. It has been demonstrated that in *A. fumigatus* the same activity was present when the protein was either released in the culture medium (in absence of GPI anchor) or anchored to the plasma membrane.

This result suggests that expression of the glucanosyltransferase could be done in vectors for secreted expression. The *Pichia pastoris* expression system manufactured by Invitrogen was selected. This system was previously used with another *A. fumigatus* protein of 88 kDa and it was confirmed that Pichia conserved very well the glycosylation site of the native protein.

The vector used in pPICZα (In Vitrogen) for secretion with a mye epitope and six tandem histidine residues for easy purification. The C terminal sequence responsible for GPI-anchoring is removed before subcloning in pPICZα in order to obtain a truncated secreted protein enzymatically active.

This recombinant protein is used for the screening of the antifungal drugs. Inhibition of the enzymatic activity can be monitored by HPLC detection of the absence of cleavage and further elongation of any β-(1–3) laminarioligosaccharide of dp>=10 in presence of the p49 of *A. fumigatus*.

Absence of motility of the laminarioligosaccharide substrate monitored by Thin Layer Chromatography visualized by conventional charring or directly after tagging the reducing end with a chromogenic or fluorogenic radical can be the technical basis for an automated screen.

Since the product of the β-(1–3) glucanosyltransferase becomes insoluble in aqueous, due to the elongation of the β-glucan chain, the absence of precipitation of any product after prolonged incubation using a radiolabelled substrate could also be used for drug screening.

TABLE

Transferase reaction with the initial rate of formation of the transfer product $$E - rG_{12} \rightarrow E.G_6 + rG_6$$
$$\rightarrow E.G_5 + rG_7$$
$$E.G_6 + rG_{12} \rightarrow E + rG_{18}$$
$$E.G_5 + rG_{12} \rightarrow E + rG_{17}$$

---

We claim:

1. A purified nucleic acid fragment encoding a protein having a β-(1–3) glycosyl transferase activity and having sequence ID NO: 2 or 3.

2. A purified genomic DNA fragment able to encode a protein of sequence SEQ ID No: 2.

3. *E. coli* strain deposited with the CNCM under the deposit number I-1763 transformed with sequence SEQ ID No: 1.

4. *E. coli* strain deposited with the CNCM under the number I-1762 transformed with a complementary DNA sequence SEQ ID No: 2.

* * * * *